(12) United States Patent
Allen, Sr.

(10) Patent No.: US 7,104,976 B1
(45) Date of Patent: Sep. 12, 2006

(54) SANITARY DEVICE FOR MEN AND METHOD OF USING

(76) Inventor: Josephus D. Allen, Sr., P.O. Box 47049, District Heights, MD (US) 20753

( * ) Notice: Subject to any disclaimer, the term of this patent is extended or adjusted under 35 U.S.C. 154(b) by 335 days.

(21) Appl. No.: 10/651,739

(22) Filed: Aug. 29, 2003

(51) Int. Cl.
*A61F 13/15* (2006.01)
*A61F 13/20* (2006.01)

(52) U.S. Cl. .................. 604/385.03; 604/358; 604/387
(58) Field of Classification Search ........... 604/385.01, 604/358, 385.03, 385.09, 385.11, 386–387; 119/867–869, 161–162, 169
See application file for complete search history.

(56) References Cited

U.S. PATENT DOCUMENTS

| | | | | | |
|---|---|---|---|---|---|
| 1,979,983 | A | * | 11/1934 | Meek | 2/53 |
| 2,244,656 | A | * | 6/1941 | Asch | 2/49.2 |
| 3,286,279 | A | * | 11/1966 | Brown | 2/49.2 |
| 3,979,776 | A | * | 9/1976 | Gruenwald | 2/49.1 |
| 4,125,656 | A | * | 11/1978 | Creamer | 4/251.1 |
| 4,207,633 | A | * | 6/1980 | Smith et al. | 5/632 |
| 4,589,877 | A | * | 5/1986 | Sivilich | 604/385.01 |
| 4,627,846 | A | * | 12/1986 | Ternstrom | 604/349 |
| 5,176,672 | A | * | 1/1993 | Bruemmer et al. | 604/385.19 |
| 5,881,382 | A | * | 3/1999 | Bernard et al. | 2/49.1 |
| 5,960,471 | A | * | 10/1999 | Burton | 2/48 |

\* cited by examiner

*Primary Examiner*—Michele Kidwell

(57) ABSTRACT

A new and improved sanitary device and method of using the device by a male wearer is disclosed. The sanitary device comprises a U-shaped pad having a rear and two side arms extending away in parallel from the rear zone. The two side arms define a penile/scrotum collar. When the rear zone is placed around the buttocks area of the male wearer the two side arms are graspable by the male wearer so that the penile/scrotum collar may be pulled underneath the penis and scrotum area of the male wearer. In this manner of wearing the sanitary device underneath the penis and scrotum, physical restraints on the penis and scrotum are minimized while simultaneously allowing fluids to be adsorbed by the U-shaped pad. The U-shape pad also having a top layer, a middle layer, and a bottom layer. The top layer comprising a liquid-pervious material intended to be facing away from the torso of the male wearer. The middle layer comprises a liquid adsorbent material. The bottom layer comprises a liquid pervious material or a liquid impervious layer, in which the exposed surface of the bottom layer is intended to contact torso of the male wearer. The method of using comprises obtaining, opening, removing, discarding, putting, detaching, throwing away, orienting, adhering, pulling, securing, clipping, allowing, un-clipping, un-securing, dangling, un-adhering, disposing.

2 Claims, 3 Drawing Sheets

SANITARY DEVICE FOR MEN AND METHOD OF USING

FIELD OF THE INVENTION

The present invention relates in general to devices for absorbing body exudate, more particularly to an improved moisture absorbent shield adapted specifically for use by male wearers, and a method of using such a device.

DESCRIPTION OF THE PRIOR ART

Incontinence is a malody from which a great many elderly and ill individuals suffer. The inability to restrain or control the discharge of waste material from the body, particularly urine, is a problem that often cannot be remedied and, therefore, it is necessary to provide the incontinent individual with a means for containing the discharge, thereby enabling the individual to lead a relatively normal life.

One successful approach to this problem has been the use of incontinence garments such as briefs or the like, which can be used and reused. Such garments are provided with a pocket-like structure into which a disposable moisture absorbent incontinence pad can be inserted. The pad, once it becomes moisture laden, is removed from the garment and a new pad is substituted in its place. Alternatively, a disposable incontinence pad is provided which is adapted for use with normal underclothing and is attached or fixed thereto by strips of adhesive tape or other suitable means.

However, for lightly incontinent males the above-described pads are an impediment to normal urination. A pad is required for such individuals but one that is adapted to accomodate normal urination as well.

A wide variety of sanitary devices is currently available on the commercial market and an even larger number of these types of devices are known in the art of sanitary devices, for example, the incontinent pad disclosed by Hokanson in U.S. Pat. No. 3,968,798; the crush resistant adhesively-attached absorbent product disclosed by Bradstreet and Roller in U.S. Pat. No. 4,217,901; the moisture absorbent pad disclosed by Fowler in U.S. Pat. No. 4,372,309; the sanitary pads for men disclosed by Lipner in U.S. Pat. No. 4,576,599; the male incontinence device disclosed by Sivilich in U.S. Pat. No. 4,589,877; the incontinence guard for men disclosed by Runeman and Ronnberg in U.S. Pat. No. 5,486,168; the method of manufacturing incontinence articles for males disclosed by Sherrod, LeMahieu and Rooyakkers in U.S. Pat. No. 5,558,734; the absorbent structure in an absorbent product such as an absorbent pants, diaper, incontinence protector, sanitary napkin, panty liner, dressing or the like disclosed by Gustafsson, Buschka, Kalentun, and Schmid in U.S. Pat. No. 6,156,951; the absorbent article having increased front portion stiffness disclosed by Gjorklund, Widlund, Samuelsson, Drevik and Gustafsson in U.S. Pat. No. 6,325,786B1; the incontinence diaper disclosed by Minot in U.S. Pat. No. D302,854; the male incontinence pad disclosed by Anderson in U.S. Pat. No. D434,144; and the sanitary napkin for men in U.S. Pat. No. D435,907S.

While all of the above-described devices fulfill their respective, particular objectives and requirements, the aforementioned patents do not describe a sanitary device having a U-shaped pad comprising a rear zone and two side arms extending away in parallel from the rear zone, in which the two side arms define a penile/scrotum collar. These features would specifically match the user's particular individual needs of making it possible to wearing a sanitary device underneath the penis and scrotum, in order to minimize any physical restraints on the penis and scrotum while simultaneously allowing fluids to be adsorbed by such a device. The above-described patents make no provision for sanitary device comprising a U-shaped pad having a rear zone and two side arms.

Therefore, a need exists for a new and improved sanitary device that can be used for wearing underneath the penis and scrotum, in order to minimize any physical restraints on the penis and scrotum while simultaneously allowing fluids to be adsorbed by such a device. In this respect, the sanitary device according to the present invention substantially departs from the conventional concepts and designs of the prior art, and in doing so provides an apparatus primarily developed for these purposes by providing a sanitary device having a U-shaped pad comprising a rear zone and two side arms extending away in parallel from the rear zone, in which the two side arms define a penile/scrotum collar.

SUMMARY OF THE INVENTION

The present device, according to the principles of the present invention, overcomes the shortcomings of the prior art by providing a new and improved sanitary device and method of using the device by a male wearer is disclosed. The sanitary device comprises a U-shaped pad having a rear and two side arms extending away in parallel from the rear zone. The two side arms defines a penile/scrotum collar. When the rear zone is placed around the buttocks area of the male wearer the two side arms are graspable by the male wearer so that the penile/scrotum collar may be pulled underneath the penis and scrotum area of the male wearer. In this manner of wearing the sanitary device underneath the penis and scrotum, physical restraints on the penis and scrotum are minimized while simultaneously allowing fluids to be adsorbed by the U-shaped pad. The U-shape pad also having a top layer, a middle layer, and a bottom layer. The top layer comprising a liquid-pervious material intended to be facing away from the torso of the male wearer. The middle layer comprises a liquid adsorbent material. The bottom layer comprises a liquid pervious material or a liquid impervious layer, in which the exposed surface of the bottom layer is intended to contact torso of the male wearer.

In view of the foregoing disadvantages inherent in the known type sanitary devices now present in the prior art, the present invention provides an improved sanitary device, which will be described subsequently in great detail, is to provide a new and improved sanitary device which is not anticipated, rendered obvious, suggested, or even implied by the prior art, either alone or in any combination thereof.

To attain this, the present invention essentially comprises a new and improved sanitary device and method of using the device by a male wearer is disclosed. The sanitary device comprises a U-shaped pad having a rear and two side arms extending away in parallel from the rear zone. The two side arms define a penile/scrotum collar. When the rear zone is placed around the buttocks area of the male wearer the two side arms are graspable by the male wearer so that the penile/scrotum collar may be pulled underneath the penis and scrotum area of the male wearer. In this manner of wearing the sanitary device underneath the penis and scrotum, physical restraints on the penis and scrotum are minimized while simultaneously allowing fluids to be adsorbed by the U-shaped pad. The U-shape pad also having a top layer, a middle layer, and a bottom layer. The top layer comprising a liquid-pervious material intended to be facing away from the torso of the male wearer. The middle layer comprises a liquid adsorbent material. The bottom layer either comprising a liquid pervious material or a liquid impervious layer, in which the exposed surface of the bottom layer is intended to contact torso of the male wearer.

There has thus been outlined, rather broadly, the more important features of the invention in order that the detailed description thereof that follows may be better understood, and in order that the present contribution of the art may be better appreciated.

The invention may also include an optional adhesive zone, a paper strip and a storage bag. There are of course, additional features of the invention that will be described hereinafter and which will form the subject matter of the claims attached.

Numerous objects, features and advantages of the present invention will be readily apparent to those of ordinary skill in the art upon reading of the following detailed description of presently preferred, but nonetheless illustrative, embodiments of the present invention when taken in conjunction with the accompany drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved sanitary device that has all the advantages of the prior art sanitary device and none of the disadvantages.

It is another object of the present invention to provide a new and improved sanitary device that may be easily and efficiently manufactured and marketed.

An even further object of the present invention is to provide a new and improved sanitary device that has a low cost of manufacture with regard to both materials and labor, and which accordingly is then susceptible of low prices of sale to the consuming public, thereby making such multipurpose storage unit and system economically available to the buying public.

Still another object of the present invention is to provide a new sanitary device that provides in the apparatuses and methods of the prior art some of the advantages thererof, while simultaneously overcoming some of the disadvantages normally associated therewith.

Even still another object of the present invention is to provide a sanitary device having a U-shaped pad having a rear and two side arms extending away in parallel from the rear zone, in which the two side arms defining a penile/scrotum collar. This makes it possible to wearing the sanitary device underneath the penis and scrotum, so that any physical restraints on the penis and scrotum are minimized while simultaneously allowing fluids to be adsorbed by the U-shaped pad.

Lastly, it is an object of the present invention to provide a new and improved method of using the device comprises obtaining, opening, removing, discarding, putting, detaching, throwing away, orienting, adhering, pulling, securing, clipping, allowing, un-clipping, un-securing, dangling, un-adhering, disposing.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompany drawings and description matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various figures.

DETAILED DESCRIPTION OF THE PREFERRED EMBODIMENT

Figure 1:
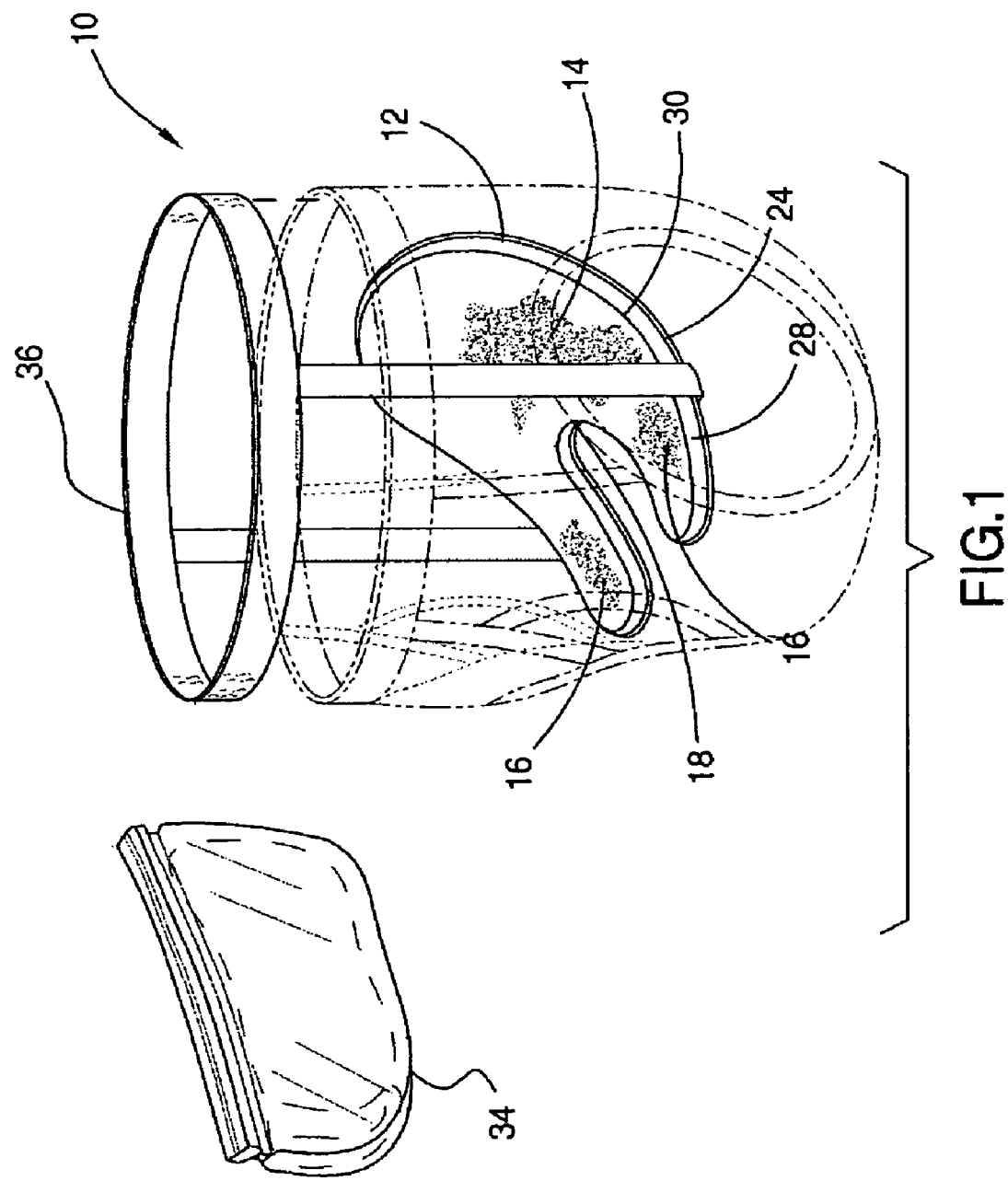
FIG. 1 is a perspective view of a preferred embodiment of the sanitary device constructed in accordance with the principles of the present invention.
Figure 2:
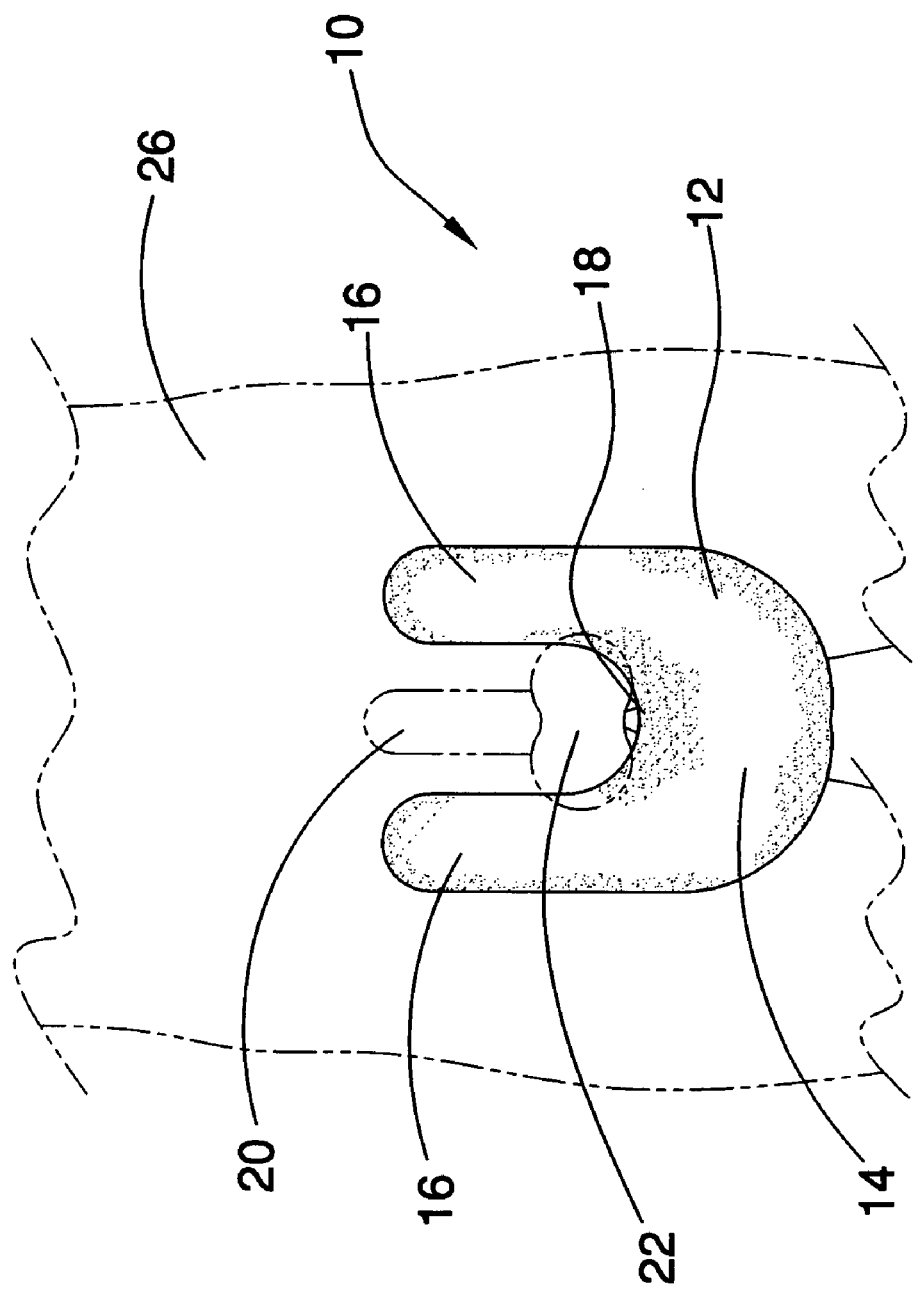
FIG. 2 is a frontal view of a preferred embodiment of the sanitary device of the present invention.
Figure 3:
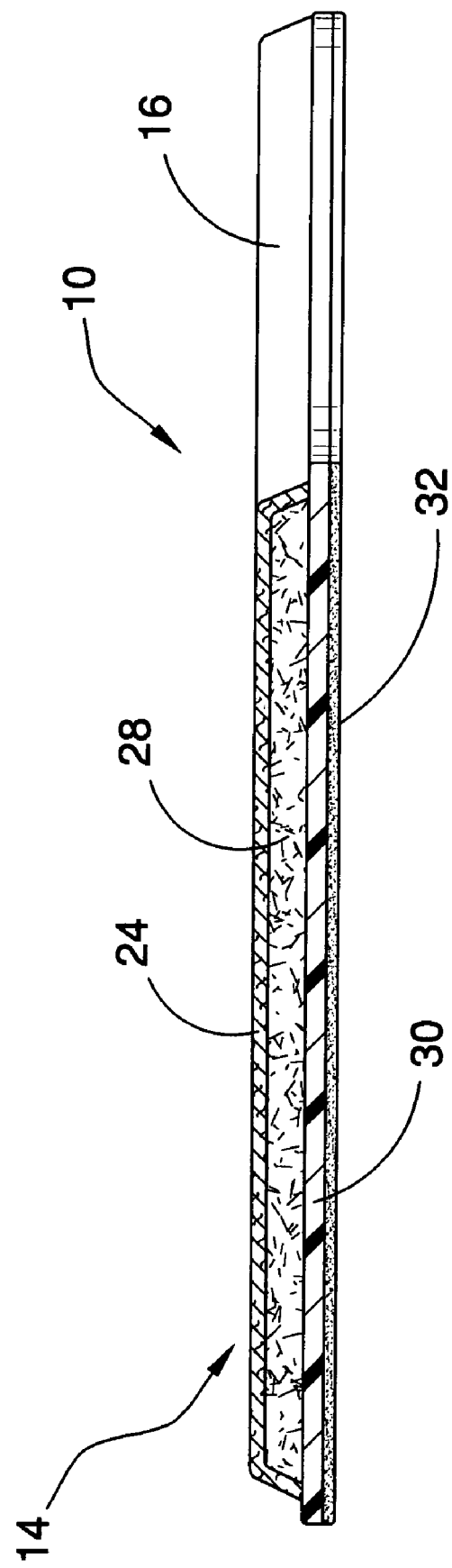
FIG. 3 is a cross sectional side view of a preferred embodiment of the sanitary device of the present invention.

Referring now to the drawings, and in particular FIGS. 1 to 3 thereof, one preferred embodiment of the present invention is shown and generally designated by the reference numeral 10. One preferred embodiment of the sanitary device 10 for use by a male wearer, the sanitary device 10 comprising a U-shape pad 12 having a rear zone 14, two side arms 16, a top layer 24, a middle layer 28, and a bottom layer 30. The U-shape pad 12 having a rear zone 14 and two side arms 16 attached to the rear zone 14 extending away in parallel from the rear zone 14. The two side arms 16 defining a penile/scrotum collar 18. The rear zone 14 is for placement around the buttocks area of the male wearer and the two side arms 16 are graspable by the male wearer to pull the penile/scrotum collar 18 underneath the penis 20 and scrotum 22 area of the male wearer, whereby minimizing physical restraints from the sanitary device 10 on the penis 20 and scrotum 22 of the male wearer. The top layer 24 comprising a liquid-pervious material intended to be facing away from the torso 26 of the male wearer. The middle layer 28 attached underneath of the top layer 24, the middle layer 28 comprising a liquid adsorbent material. The bottom layer 30 attached underneath of the middle layer 28 having an exposed surface intended to be contacting a portion of the torso 26 of the male wearer.

Another preferred embodiment of the sanitary device 10 comprises: a U-shape pad 12, a belt 36 and a storage bag 34. The U-shape pad 12 having: a rear zone 14, two side arms 16, a top layer 24, a middle layer 28, a bottom layer 30, an adhesive zone 32, and a paper strip. The rear zone 14 and two side arms 16 are attached to the rear zone 14 and the two side arms 16 extending away in parallel from the rear zone 14. The two side arms 16 define a penile/scrotum collar 18, in which the rear zone 14 is for placement around the buttocks area of the male wearer so that the two side arms 16 are graspable by the male wearer in order to pull the penile/scrotum collar 18 underneath the penis 20 and scrotum 22 area of the male wearer. In this manner of usage, the U-shape pad 12 minimizes any physical restraints from the sanitary device 10 on the penis 20 and scrotum 22 of the male wearer. The top layer 24 comprises a liquid-pervious material intended to be facing away from the torso 26 of the male. The middle layer 28 attached underneath of the top layer 24, the middle layer 28 comprising a liquid adsorbent material. The bottom layer 30 attached underneath of the middle layer 28 and has an exposed surface intended to be contact a portion of the torso 26 of the male wearer. The adhesive zone 32 attached to a portion of the exposed surface of the bottom layer 30, wherein the adhesive zone 32 is operable to adhere the sanitary device 10 around a portion of the torso 26 of the male wearer. The paper strip attached over the adhesive zone 32 wherein the paper strip is detachable from the adhesive zone 32 when pulled away from the sanitary device 10. The belt 36 is attachable to the sanitary device 10, in which the belt 36 is intended to be worn around the waist of the torso 26 of the male wearer. The storage bag 34 is for storing the sanitary device 10 before use in a sanitized state.

One preferred embodiment of the method of using a sanitary device 10 use by a male wearer, the method comprising the steps of: obtaining, opening, removing, discarding, putting, detaching, throwing away, orienting, adhering, pulling, securing, clipping, allowing, un-clipping, un-securing, dangling, un-adhering, disposing. The obtaining step comprises obtaining sanitary device 10 comprising: a U-shape pad 12 having: a rear zone 14 and two side arms 16 attached to the rear zone 14 extending away in parallel from the rear zone 14, the two side arms 16 defining a penile/scrotum collar 18, wherein the rear zone 14 is for placement around the buttocks area of the male wearer and the two side arms 16 are graspable by the male wearer to pull the penile/scrotum collar 18 underneath the penis 20 and scrotum 22 area of the male wearer, whereby minimizing physical restraints from the sanitary device 10 on the penis 20 and scrotum 22 of the male wearer; a top layer 24 comprising a liquid-pervious material intended to be facing away from the torso 26 of the male; a middle layer 28 attached underneath of the top layer 24, the middle layer 28 comprising a liquid adsorbent material; a bottom layer 30 attached underneath of the middle layer 28 having an exposed surface intended to be contacting a portion of the torso 26 of the male wearer; an adhesive zone 32 attached to a portion of the exposed surface of the bottom layer 30, wherein the adhesive zone 32 is operable to adhere the sanitary device 10 around a portion of the torso 26 of the male wearer; and a paper strip attached over the adhesive zone 32 wherein the paper strip is detachable from the adhesive zone 32 when pulled away from the sanitary device 10; a belt 36 attachable to the sanitary device 10, the belt 36 intended to be worn around the waist of the torso 26 of the male wearer; and a storage bag 34 for storing the sanitary device 10 before use in a sanitized state. The opening step comprises opening the storage bag 34. The removing step comprises removing the U-shape pad 12 and the belt 36. The discarding step comprises discarding the storage bag 34. The putting step comprises putting on the belt 36 around the waist of the torso 26 of the male wearer. The detaching step comprises detaching the paper strip from the adhesive zone 32 on the U-shape pad 12. The throwing away step comprises throwing away the detached paper strip. The orienting step comprises orienting the bottom layer 30 of the U-shape pad 12 to face the torso 26 of the male wearer. The adhering step comprises adhering the rear zone 14 of the U-shaped pad onto the buttocks area of the male wearer while the two arms of the U-shaped pad dangle between the legs of the male wearer. The pulling step comprises pulling on the two arms of the U-shaped pad so that the penile/scrotum collar 18 is positioned underneath the penis 20 and scrotum 22 area of the male wearer. The securing step comprises securing the two arms to a portion of the torso 26 of the male wearer above the penis 20 of the male wearer. The clipping step comprises clipping the two arms and the rear zone 14 to the belt 36 worn around the waist of the male wearer. The allowing step comprises allowing the U-shape pad 12 to adsorb liquids exudated from the male wearer. The un-clipping step comprises un-clipping the two arms and the rear zone 14 from the belt 36 worn around the waist of the male wearer. The un-securing step comprises un-securing the two arms from the portion of the torso 26 of the male wearer above the penis 20 of the male wearer. The dangling step comprises dangling the two arms of the U-shaped pad between the legs of the male wearer. The un-adhering step comprises un-adhering the rear zone 14 of the U-shaped pad from the buttocks area of the male wearer while the two arms of the U-shaped pad dangle between the legs of the male wearer. The disposing step comprises disposing the used U-shaped pad.

The sanitary device 10 may be configured in any number of different configurations. One preferred configuration is that the U-shape pad 12 is seamless.

The top layer 24 may comprise any number of materials as long as the top layer 24 is liquid pervious. One preferred configuration of the top layer 24 is that it comprises a woven cotton fabric.

The middle layer 28 may comprise any number of commercially available materials as long as these materials are able to adsorb water. One preferred configuration of the material comprising the middle layer 28 is that the middle layer 28 comprises a super adsorbent material for immobilizing absorbed liquid as described in the male incontinence device disclosed by Sivilich in U.S. Pat. No. 4,589,877, hereinafter incorporated by reference. The super adsorbent material may comprise the starch polymer known as DWAL (trademark of Dow Chemical) or a modified acrylic polymer known as GELOK 4000 (trademark of Gelok International). Another preferred configuration of the material comprising the middle layer 28 is that it further comprises a laminate of a base or carrier and a polymer which gels when wet along with the above referenced super adsorbent material in which the polymer is a starch polymer or an acrylic polymer. Yet another preferred configuration of the middle layer 28 comprises a hydrocolloid material being capable of absorbing water in an amount which is at least ten times its own weight in dry form, as discussed by Bradstreet and Roller in the crush resistant adhesively-attached absorbent product disclosed in U.S. Pat. No. 4,217,901, hereinafter this reference is incorporated by reference. The middle layer 28 can comprises grafted polysaccharide consisting of a cellulose backbone having grafted thereon hydrophillic chains as well as hydrocolloid material chosen from the group consisting of carboxylated, phosphonoalkylates, sulphoaalkylated and phosphorylated polysaccharides. Still yet another preferred configuration of the middle layer 28 comprises a first relatively thick adsorbent portion, and a super absorbent layer for immobilizing absorbed liquid, also disclosed by Sivilich in U.S. Pat. No. 4,589,877, in which the first relatively thick adsorbent portion comprises fluffed wood pulp. The first relatively thick adsorbent portion may further comprise a polymeric composition intermixed with the fluffed wood pulp selected from the group consisting of starch polymer, acrylic based polymer, meltblown polyethylene fibers and meltblown polypropylene fibers.

The bottom layer 30 comprises either a moisture impermeable layer or a second liquid-pervious material. In the moisture impermeable layer configuration the bottom layer 30 may comprise a polyethylene film. When the bottom layer 30 comprises a second liquid-pervious material the liquid pervious material may comprise a woven cotton fabric.

An optional adhesive zone 32 may be added to the sanitary device 10. The adhesive zone 32 attached to a portion of the exposed surface of the bottom layer 30, wherein the adhesive zone 32 is operable to adhere the sanitary device 10 around a portion of the torso 26 of the male wearer. An optional paper strip may further be added onto the optional adhesive zone 32. The paper strip attached over the adhesive zone 32 wherein the paper strip is detachable from the adhesive zone 32 when pulled away from the sanitary device 10.

An optional storage bag 34 may be added to the sanitary device 10, in which the storage bag 34 is for storing the sanitary device 10 before use in a sanitized state.

An optional belt 36 may also be added to the sanitary device 10, in which the belt 36 is attachable to the sanitary device 10. The belt 36 intended to be worn around the waist of the torso 26 of the male wearer.

Referring now to FIG. 1, which depicts a perspective view of a preferred embodiment of the sanitary device 10 comprising a U-shape pad 12 having a rear zone 14, two side arms 16, a top layer 24, a middle layer 28, and a bottom layer 30. The U-shape pad 12 having a rear zone 14 and two side arms 16 attached to the rear zone 14 extending away in parallel from the rear zone 14. The two side arms 16 defining a penile/scrotum collar 18.

Referring now to FIG. 2, which is a frontal view of a preferred embodiment of the sanitary device 10 comprising a U-shape pad 12 having a rear zone 14, two side arms 16, a top layer 24, a middle layer 28, and a bottom layer 30. The U-shape pad 12 having a rear zone 14 and two side arms 16 attached to the rear zone 14 extending away in parallel from the rear zone 14. The two side arms 16 defining a penile/scrotum collar 18. The rear zone 14 is for placement around the buttocks area of the male wearer and the two side arms 16 are graspable by the male wearer to pull the penile/scrotum collar 18 underneath the penis 20 and scrotum 22 area of the male wearer, whereby minimizing physical restraints from the sanitary device 10 on the penis 20 and scrotum 22 of the male wearer.

Referring now to FIG. 3 displaying a cross sectional side view of a preferred embodiment of the sanitary device 10 comprising a top layer 24, a middle layer 28, a bottom layer 30, and an adhesive zone 32. The top layer 24 comprises a liquid-pervious material intended to be facing away from the torso 26 of the male. The middle layer 28 attached underneath of the top layer 24, the middle layer 28 comprising a liquid adsorbent material. The bottom layer 30 attached underneath of the middle layer 28 and has an exposed surface intended to be contact a portion of the torso 26 of the male wearer. The adhesive zone 32 attached to a portion of the exposed surface of the bottom layer 30, wherein the adhesive zone 32 is operable to adhere the sanitary device 10 around a portion of the torso 26 of the male wearer.

As to the manner of usage and operation of the present invention, the same should be apparent from the above description. Accordingly, no further discussion relating to the manner of usage and operation will be provided.

While a preferred embodiment of the sanitary device has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

With respect to the above description then, it is to be realized that the optimum dimensional relationships for the parts of the invention, to include variations in size materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A sanitary device use by a male wearer, said sanitary device comprising:

a U-shape pad having:

a rear zone and two side arms attached to said rear zone extending away in parallel from said rear zone, said two side arms defining a penile/scrotum collar, wherein said rear zone is for placement around the buttocks area of the male wearer and said two side arms are graspable by the male wearer to pull said penile/scrotum collar underneath the penis and scrotum area of the male wearer, whereby minimizing physical restraints from said sanitary device on the penis and scrotum of the male wearer;

a top layer comprising a liquid-pervious material intended to be facing away from the torso of the male;

a middle layer attached underneath of said top layer, said middle layer comprising a liquid adsorbent material;

a bottom layer attached underneath of said middle layer having an exposed surface intended to be contacting a portion of the torso of the male wearer;

an adhesive zone attached to a portion of the exposed surface of said bottom layer, wherein said adhesive zone is operable to adhere said sanitary device around a portion of the torso of the male wearer; and a paper strip attached over said adhesive zone wherein said paper strip is detachable from said adhesive zone when pulled away from said sanitary device;
a belt attachable to said sanitary device, said belt intended to be worn around the waist of the torso of the male wearer; and
a storage bag for storing said sanitary device before use in a sanitized state.

2. A method of using a sanitary device use by a male wearer, said method comprising the steps of:

obtaining sanitary device comprising:
  a U-shape pad having:
    a rear zone and two side arms attached to said rear zone extending away in parallel from said rear zone, said two side arms defining a penile/scrotum collar, wherein said rear zone is for placement around the buttocks area of the male wearer and said two side arms are graspable by the male wearer to pull said penile/scrotum collar underneath the penis and scrotum area of the male wearer, whereby minimizing physical restraints from said sanitary device on the penis and scrotum of the male wearer;
    a top layer comprising a liquid-pervious material intended to be facing away from the torso of the male;
    a middle layer attached underneath of said top layer, said middle layer comprising a liquid adsorbent material;
    a bottom layer attached underneath of said middle layer having an exposed surface intended to be contacting a portion of the torso of the male wearer;
    an adhesive zone attached to a portion of the exposed surface of said bottom layer, wherein said adhesive zone is operable to adhere said sanitary device around a portion of the torso of the male wearer; and
    a paper strip attached over said adhesive zone wherein said paper strip is detachable from said adhesive zone when pulled away from said sanitary device;
  a belt attachable to said sanitary device, said belt intended to be worn around the waist of the torso of the male wearer; and
  a storage bag for storing said sanitary device before use in a sanitized state;
opening the storage bag;
removing the U-shape pad and the belt;
discarding the storage bag,
putting on the belt around the waist of the torso of the male wearer;
detaching the paper strip from the adhesive zone on said U-shape pad;
throwing away the detached paper strip;
orienting the bottom layer of the U-shape pad to face the torso of the male wearer;
adhering the rear zone of the U-shaped pad onto the buttocks area of the male wearer while the two arms of the U-shaped pad dangle between the legs of the male wearer;
pulling on the two arms of the U-shaped pad so that the penile/scrotum collar is positioned underneath the penis and scrotum area of the male wearer;
securing the two arms to a portion of the torso of the male wearer above the penis of the male wearer;
clipping the two arms and the rear zone to the belt worn around the waist of the male wearer;
allowing the U-shape pad to adsorb liquids exudated from the male wearer;
un-clipping the two arms and the rear zone from the belt worn around the waist of the male wearer;
un-securing the two arms from the portion of the torso of the male wearer above the penis of the male wearer;
dangling the two arms of the U-shaped pad between the legs of the male wearer;
un-adhering the rear zone of the U-shaped pad from the buttocks area of the male wearer while the two arms of the U-shaped pad dangle between the legs of the male wearer; and
disposing the used U-shaped pad.

* * * * *